United States Patent [19]
Griffiths et al.

[11] Patent Number: 5,958,408
[45] Date of Patent: *Sep. 28, 1999

[54] DELIVERY OF DIAGNOSTIC AND THERAPEUTIC AGENTS TO A TARGET SITE

[75] Inventors: Gary L. Griffiths, Morristown; Hans J. Hansen, Mystic Island; Serengulam V. Govindan, Summit; Habibe Karacay, Clifton, all of N.J.

[73] Assignee: Immunomedics, Inc., Morris Plains, N.J.

[ * ] Notice: This patent is subject to a terminal disclaimer.

[21] Appl. No.: 08/972,037

[22] Filed: Nov. 17, 1997

Related U.S. Application Data

[63] Continuation of application No. 08/731,107, Oct. 9, 1996, which is a continuation-in-part of application No. 08/486,166, Jun. 7, 1995, abandoned.

[51] Int. Cl.$^6$ .......... A61K 39/395; C12N 15/11; C07M 21/00; C07K 16/00
[52] U.S. Cl. .......... 424/133.1; 530/387.2; 530/387.3; 514/2; 514/44; 424/1.11; 424/1.41; 424/1.57; 424/1.65; 424/1.69; 424/1.73; 424/9.3; 424/9.34; 424/9.341; 424/9.35; 424/9.351; 424/9.36; 424/9.6; 424/178.1; 424/183.1; 424/900; 424/133.3
[58] Field of Search .......... 424/1.11, 1.41, 424/1.57, 1.65, 1.69, 1.73, 9.3, 9.34, 9.341, 9.35, 9.351, 9.36, 9.6, 178.1, 183.1, 900, 131.1, 133.1; 530/387.2, 387.3; 514/2, 44

[56] References Cited

U.S. PATENT DOCUMENTS

| | | | |
|---|---|---|---|
| 4,624,846 | 11/1986 | Goldenberg | 424/1.11 |
| 5,525,338 | 6/1996 | Goldenberg | 424/178.1 |
| 5,641,625 | 6/1997 | Ecker et al. | 435/6 |
| 5,733,523 | 3/1998 | Kuijpers et al. | 424/1.73 |

FOREIGN PATENT DOCUMENTS

| 10140 | 11/1989 | WIPO . |
|---|---|---|
| 04000 | 2/1996 | WIPO . |

OTHER PUBLICATIONS

Bos et al, Cancer Research vol. 54 p. 3479, Jul. 1994.

D.L. Urdal, "Tumor–Associated Ganglio–N–Triosylceramide", The Journal of Biological Chemistry, vol. 255, No. 21, Nov. 1980, pp. 10509–10516.

Goodwin, et al., "Pharmacokinetics of Pretargeted Monoclonal Antibody 2D12.5 and $^{88}$Y–Janus–2–(p–Nitrobenzyl)–1,4,7,10–tetrazacyclododecanetetraacetic Acid (DOTA) in BALB/c Mice with KHJJ Mouse Adenocarcinoma: A Modelfor $^{90}$Y Radioimmunotherapy", Cancer Research, vol. 54, 1994, pp. 5937–5946.

S. Hakomori, et al., "Glycolipid Tumor Cell Markers and their Monoclonal Antibodies: Drug Targeting and Immunosuppression", pp. 177–199. (1983).

Illustrated Dictionary of Immunology, pp. 24, 1995.

*Primary Examiner*—Julie Reeves
*Attorney, Agent, or Firm*—Foley & Lardner

[57] ABSTRACT

An improvement in in vivo pretargeting methods for delivering diagnostic or therapeutic agents to a target site in a mammal uses a clearing agent that binds to the target-binding site of the targeting species, whereby non-bound primary targeting species is cleared from circulation but the clearing agent does not remove the bound primary targeting species. Anti-idiotype antibodies and antibody fragments are preferred clearing agents. Fast clearance is achieved by glycosylating the clearing agent with sugar residues that bind to the hepatic asialoglycoprotein receptor.

24 Claims, No Drawings

DELIVERY OF DIAGNOSTIC AND THERAPEUTIC AGENTS TO A TARGET SITE

CROSS-REFERENCE TO RELATED APPLICATION

This application is a continuation of application Ser. No. 08/731,107, filed Oct. 9, 1996, which is a continuation-in-part of Ser. No. 08/486,166, filed Jun. 7, 1995 now abandoned.

BACKGROUND OF THE INVENTION

1—Field of the Invention

The present invention relates to improved clearing agents for use in targeting diagnostic or therapeutic agents to a target site in a mammal. The present invention also relates to improved methods for diagnosing or treating patients using improved clearing agents.

2—Description of Related Art

The detection of a target site benefits from a high signal-to-background ratio of detection agent. Therapy benefits from as high an absolute accretion of therapeutic agent at the target site as possible, as well as a reasonably long duration of uptake and binding. In order to improve the targeting ratio and amount of agent delivered to a target site, the use of targeting vectors comprising diagnostic or therapeutic agents conjugated to a targeting moiety for preferential localization has long been known.

Examples of targeting vectors include diagnostic or therapeutic agent conjugates of targeting moieties such as antibody or antibody fragments, cell- or tissue-specific peptides, and hormones and other receptor-binding molecules. For example, antibodies against different determinants associated with pathological and normal cells, as well as associated with pathogenic microorganisms, have been used for the detection and treatment of a wide variety of pathological conditions or lesions. In these methods., the targeting antibody is directly conjugated to an appropriate detecting or therapeutic agent as described, for example, in Hansen et al., U.S. Pat. No. 3,927,193 and Goldenberg, U.S. Pat. Nos. 4,331,647, 4,348,376, 4,361,544, 4,468,457, 4,444,744, 4,460,459, 4,460,561, 4,624,846 and 4,818,709, the disclosures of all of which are incorporated herein by reference.

One problem encountered in direct targeting methods, i.e., in methods wherein the diagnostic or therapeutic agent (the "active agent") is conjugated directly to the targeting moiety, is that a relatively small fraction of the conjugate actually binds to the target site, while the majority of conjugate remains in circulation and compromises in one way or another the function of the targeted conjugate. In the case of a diagnostic conjugate, for example, a radioimmunoscintigraphic or magnetic resonance imaging conjugate, non-targeted conjugate which remains in circulation can increase background and decrease resolution. In the case of a therapeutic conjugate having a very toxic therapeutic agent, e.g., a radioisotope, drug or toxin, attached to a long-circulating targeting moiety such as an antibody, circulating conjugate can result in unacceptable toxicity to the host, such as marrow toxicity or systemic side effects.

Pretargeting methods have been developed to increase the target:background ratios of the detection or therapeutic agents. Examples of pre-targeting and biotin/avidin approaches are described, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; Stickney et al., Cancer Res. 51:6650, 1991; and Yuan et al., Cancer Res. 51:3119, 1991; all of which are incorporated by reference herein in their entirety.

In pretargeting methods, a primary targeting species (which is not bound to a diagnostic or therapeutic agent) comprising a first targeting moiety which binds to the target site and a binding site that is available for binding by a subsequently administered second targeting species is targeted to an in vivo target site. Once sufficient accretion of the primary targeting species is achieved, a second targeting species comprising a diagnostic or therapeutic agent and a second targeting moiety, which recognizes the available binding site of the primary targeting species, is administered.

An illustrative example of pretargeting methodology is the use of the biotin-avidin system to administer a cytotoxic radioantibody to a tumor. In a typical procedure, a monoclonal antibody targeted against a tumor-associated antigen is conjugated to avidin (or biotin) and administered to a patient who has a tumor recognized by the antibody. Then the therapeutic agent, e.g., a chelated radionuclide covalently bound to biotin (or avidin), is administered. The radionuclide, via its attached biotin (or avidin), is taken up by the antibody-avidin (or -biotin) conjugate pretargeted to the tumor.

Pretargeting is an approach which offers certain advantages over the use of direct targeting methods. For example, use of the pretargeting approach for the in vivo delivery of radionuclides to a target for therapy, e.g., radioimmunotherapy, reduces the marrow toxicity caused by prolonged circulation of a radioimmunoconjugate. This is because the radioisotope is delivered as a rapidly clearing, low molecular weight chelate rather than directly conjugated to a primary targeting molecule, which is often a long-circulating species.

One problem encountered with two-step pretargeting methods is that circulating primary targeting species (antibody-avidin or -biotin conjugate, for example) interferes with the targeting of active agent species (biotin- or avidin-active agent conjugate) at the target site by competing for the binding sites on the active agent-conjugate. This problem typically is avoided or minimized by the use of a three-step approach wherein a clearing agent is administered as an intermediate step of the above two-step approach. The clearing agent binds and removes circulating primary conjugate which is not bound at the target site.

Paganelli et al. (J. Nucl. Med. 31:735, 1990 and Cancer Res. 51:5960, 1991) disclose a 3-step approach wherein a biotinylated antibody is administered, followed by cold, i.e., non-labeled and non-conjugated, avidin to clear nontargeted antibody. Radiolabeled biotin is then administered which binds to the avidin retained in the body, presumably where the avidin has complexed to the biotinylated antibody.

When antibody-avidin is used as the primary targeting moiety, excess circulating conjugate is cleared by injecting a biotinylated polymer such as biotinylated human serum albumin. This type of agent forms a high molecular weight species with the circulating avidin-antibody conjugate which is quickly recognized by the hepatobiliary system and deposited primarily in the liver.

To speed up this hepatobiliary recognition process, the clearing agent may be substituted with sugar residues, primarily galactose, such that the galactosylated complex is recognized by the asialoglycoprotein receptors in the liver. By using a galactosylated biotin-protein, substantially all circulating streptavidin-antibody and galactosylated biotin-protein is deposited into the liver on the first pass through, making the clearing process very fast and efficient. With circulating avidin conjugate removed, excess biotin-chelate-radionuclide is rapidly eliminated, preferably renally. Because the radionuclide spends a very short time in circulation, considerably less marrow toxicity to the patient is seen compared to when the radionuclide is attached directly to the antibody.

Examples of this methodology are disclosed, e.g., in Axworthy et al., PCT Application No. WO 93/25240; Paganelli et al., "Monoclonal Antibody Pretargeting Techniques For Tumour Localization: The Avidin-Biotin System", Nucl. Med. Comm., Vol. 12:211–234, (1991); Oehr et al., "Streptavidin And Biotin As Potential Tumor Imaging Agents", J. Nucl. Med., Vol. 29:728–729, (1988); Kalofonos et al., "Imaging Of Tumor In Patients With Indium-111-Labeled Biotin And Streptavidin-Conjugated Antibodies: Preliminary Communication", J. Nucl. Med., Vol 31:1791–1796, (1990); Goodwin et al., "Pre-Targeted Immunoscintigraphy Of Murine Tumors With Indium-111-Labeled Bifunctional Haptens", J. Nucl. Med., Vol. 29:226–234, (1988). Improved pretargeting methods using the biotin-avidin system are disclosed, e.g., in U.S. Pat. Nos. 5,525,338, 5,736,119, 5,846,741 and 5,482,698 and co-pending U.S. patent applications Ser. Nos. 08/486,166, and 08/688,781, the disclosures of which are incorporated by reference herein in their entirety.

Pretargeting as it has been practiced to date suffers from certain drawbacks. First among these is the very low amount of radionuclide delivered to the target site compared to when the radionuclide is directly attached to an antibody. Using the above example, the problem of low target accretion is exacerbated by the choice of the clearing agent used for the avidin-antibody conjugate. In that approach, it has been found that the clearing agent also removes antibody-avidin conjugate previously bound to the target site. This substantially reduces the amount of antibody-avidin at the target, typically by 50% or more. Further, the use of a biotinylated clearing agent tends to partially block remaining antibody-avidin sites at the target, thereby reducing the number of sites available for binding by the biotinylated diagnostic or therapeutic agent.

A need exists, therefore, for improved clearing agents which work efficiently and rapidly, but do not block the binding sites at the target site, and which do not remove primary conjugate localized at the target site.

SUMMARY OF THE INVENTION

One object of the present invention is to provide improved clearing agents for clearing non-targeted primary targeting species efficiently and quickly from circulation.

Another object of the present invention is to provide improved methods of in vivo diagnosis or therapy using clearing agents which efficiently clear non-localized targeting species from circulation.

These and other objects are realized by providing, in an in vivo pretargeting method for delivering a diagnostic or therapeutic agent to a target site in a mammal, wherein:

a primary targeting species is administered to the mammal which binds via a primary, target-specific binding site to the target site or to a substance produced by or associated with the target site and which comprises a second binding site which binds an active agent conjugate or an intermediate which in turn binds an active agent conjugate, sufficient time being allowed for said primary targeting species to localize at the target site;

a clearing agent is then administered that binds to the primary targeting species, sufficient time being allowed for said clearing agent to clear said primary targeting species from circulation; and an active agent conjugate, comprising a moiety that binds to the second binding site of the primary targeting species conjugated to a diagnostic or therapeutic agent, is then administered to said mammal, sufficient time being allowed for the conjugate to localize at the target site, the improvement wherein the clearing agent binds to the primary binding site of the primary targeting species, whereby substantially only non-bound primary targeting species is cleared and targeted primary targeting species is not removed from the target site, nor is the second binding site of the primary targeting species blocked by the clearing agent.

In another aspect of the present invention, the clearing agent is substituted with sugar residues, such as galactose residues, that selectively bind to the hepatic asialoglycoprotein receptor, whereby hepatic clearance is effected substantially in a single pass.

Additional objects and advantages of the invention will be set forth in part in the description that follows, and in part will be obvious from the description, or may be learned by practice of the invention. The objects and advantages may be realized and obtained by means of the processes and compositions particularly pointed out in the appended claims.

DETAILED DESCRIPTION

The following terms are used in this application:

Target site: A specific site to which a diagnostic or therapeutic agent is to be delivered, such as a cell or group of cells, tissue, organ, tumor or lesion.

Primary targeting moiety: A moiety that binds to the target site or to a substance produced by or associated with the target site via a primary binding site. For example, proteins, peptides, polypeptides, glycoproteins, lipoproteins, phospholipids, oligonucleotides, steroids, alkaloids or the like, e.g., hormones, lymphokines, growth factors, albumin, cytokines, enzymes, immune modulators, receptor proteins, antisense oligonucleotides, antibodies and antibody fragments, which preferentially bind marker substances that are produced by or associated with the target site.

Direct targeting species: A species comprising a primary targeting moiety and an active agent.

Primary targeting species: A species comprising a primary targeting moiety which binds via a primary binding site to the target site and a second binding site that is available for binding by a subsequently administered second targeting moiety. The second binding site may be a region that is a natural part of the primary targeting moiety, a modified region of the targeting moiety, or a region that is conjugated to the targeting moiety, such as a biotin or avidin molecule conjugated to the primary targeting moiety.

Second targeting moiety: A moiety that binds to the second binding site of the primary targeting species, such as an avidin or biotin moiety.

Second targeting species: Species comprising a second targeting moiety and an active agent.

Clearing agent: Agent which clears non-localized primary targeting species from circulation.

Active agent: A diagnostic or therapeutic agent.

Avidin: A family of proteins functionally defined by their ability to bind biotin with high affinity and specificity. Avidins are fairly small oligomeric proteins, made up of four identical subunits, each bearing a single binding site for biotin. Avidins can therefore bind up to four moles of biotin per mole of avidin. Avidins include proteins (a) produced by amphibians, reptiles and avians, which is present in their eggs and known as avidin, and (b) produced by a streptomyces, *Streptomyces avidinii*, and known as streptavidin. As used herein "avidin" includes all of the above proteins as well as synthetic and semisynthetic modifications thereof.

Biotin: As used herein, "biotin" includes biotin, commercial biotin products in which the biotin has been modified by the addition of alkyl groups, and biotin derivatives such as active esters, amines, hydrazides and thiol groups with the complimentary reactive groups on polymers being amines, acyl and alkyl leaving groups, carbonyl groups and alkyl halides or Michael-type acceptors.

The clearing agents of the present invention comprise a moiety which binds the primary binding site of the primary targeting species. That is, the clearing agents of the present invention bind the region of the primary targeting moiety which binds to the target site. This is in sharp contrast to previously used clearing agents which bind to other regions of the primary targeting species, such as biotin or avidin moieties conjugated to the primary targeting moiety.

The clearing agent of the present invention may comprise any molecule which is a specific binding complement to the primary binding site of the primary targeting moiety. In one embodiment of the present invention, the primary targeting species is an antibody, and the clearing agent comprises an antibody which specifically binds to the primary binding site (the paratope or antigen-binding region) of the targeting antibody, i.e., the clearing agent comprises an anti-idiotypic second antibody. Because the "anti-idiotype" antibody, as used according to the present invention, functions as a clearing agent but not necessarily as an antigen mimic, it need not bind exclusively to the paratopic region of the idiotype/targeting antibody but need only bind to a region on the antibody such that the paratope no longer can bind to the target antigen. Accordingly, the clearing agents also may be non-antibody species that bind to the primary binding site of the targeting antibody. Preferred clearing agents of the present invention include anti-idiotype monoclonal antibodies.

When non-antibody primary targeting species are used, such as small peptides, steroids, hormones, cytokines, neurotransmitters, or other targeting species which preferentially bind marker substances that are produced by or associated with the target site, the clearing agent may comprise an antibody that specifically binds to the receptor-binding site (the primary binding site) of the targeting species, i.e., to a region that blocks binding to the target receptor. A non-antibody clearing agent also may be used which binds to the primary binding site of the non-antibody primary targeting species.

Because the clearing agents of the present invention bind to the primary binding site of the primary targeting species, they can only bind circulating primary binding species, and cannot bind species already bound to the target site. The clearing agents of the present invention therefore offer distinct advantages over clearing agents currently used, and avoid the problems discussed above. That is, the present clearing agents do not block the second binding sites of the primary targeting species and do not remove bound primary targeting species from the target site.

In one advantageous embodiment of the invention, the clearing agent is conjugated to sugar residues such as galactose which bind to the hepatic asialoglycoprotein receptor, whereby the clearing agent and clearing agent-primary targeting species complexes are rapidly recognized by liver hepatocytes. Use of galactosylated clearing agents, therefore, ensures near-total hepatocytic recognition and sequestration within minutes post-injection, generally substantially in a single pass through the liver.

The degree of sugar residue modification of the clearing agent determines the blood clearance rate. It is essential that the appropriate degree of modification of the clearing agent for effective clearance with clearing agents for use with this invention. The number of sugar residues per molecule of clearing agent may be determined empirically for each specific clearing agent by routine methods well-known in the art. It is convenient to express the degree of glycosylation in terms of the percentage of lysine residues modified by addition of sugars. For anti-idiotype antibody clearing agents, it has been found that modifying about 22% of the lysine residues does not provide significantly accelerated clearance of non-localized primary targeting conjugate, whereas modifying about 48% of the lysine residues greatly accelerate clearance and modifying about 76% or more of the lysine residues results in virtually total clearance from circulation in a single pass through the liver. This will generally be true for antibody fragments as well, although the percentages may vary somewhat. The degree of glycosylation to achieve substantially complete clearance in one pass is readily determined.

Use of the biotin-avidin pair in pretargeting protocols is expected to engender the added complication of endogenous biotin binding to biotin-binding sites on an administered avidin reagent and blocking the reagent from being bound by subsequently administered biotinylated diagnostic/therapeutic agent. Biotin is ubiquitous in mammalian systems so the problem crosses species barriers, although it may be more severe in some. On the positive side, mammals cannot synthesize biotin, so it is relatively simple to induce biotin deficiency. Nude mice used in in vivo experiments for tumor pretargeting block most pretargeted streptavidin-IMMU-14 (SA-IMMU-14) within 24 h of administration. Tumor uptake of biotinylated-DTPA-indium-111 conjugate to pretargeting SA-IMMU-14 is raised significantly (19% ID/g versus 6% ID/g at 24 h post-injection) when animals are fed a biotin deficient diet for a period of one week prior to the experiment. Similar reductions in endogenous biotin levels are achieved by administration of avidin prior to pretargeting (Rosebrough, S. F. and Hartley, D. F., *Laboratory Animal Science*, 45:554–557,1995). In a preferred embodiment of the current invention, endogenous biotin levels are reduced by diet modification and/or administration of an avidin agent prior to the pretargeting protocol.

Biotin binding sites on avidin conjugated primary targeting species following delivery in the liver are advantageously blocked to prevent accumulation of the radiolabeled biotinylated chelate in the liver. One way to accomplish this objective is to attach cleavable biotins onto the clearing agent. Cleavability is easily achieved using an L-amino acid linker that is readily cleaved with biotinidase. Rapid uptake by the liver to minimize diffusion of the clearing agent into the interstitial fluid and binding/removal of primary targeted conjugate is assured by combining this approach with galactosylation of the clearing agent. It is advantageous to use a high molecular weight molecule bearing a plurality of cleavable biotin moieties and further bearing sufficient galactose residues to ensure essentially complete uptake by the liver in a single pass, the amount of said high molecular weight molecule being sufficient to deliver biotin to substantially saturate the biotin binding sites on cleared primary targeting species in the liver. The number of biotins on a clearing agent should be kept to the minimum number required since presence of a large excess of cleavable biotin may cause leakage of biotin into the blood and blockage of the biotin binding sites of the tumor. It will be appreciated that this approach must balance the advantage of blocking uptake of cytotoxic radio-labeled chelate with the potential disadvantage of blocking and/or removing targeted conjugate.

Another approach is to conjugate cleavable biotin to a molecular species that is unlikely to diffuse to the target site and that also is targeted to the liver. Such a species would be administered shortly after administration of the clearing agent and could be a polymer, e.g., aminodextran, carboxymethylcellulose, or the like, or a colloid, to which cleavable biotin and galactose residues are linked.

The clearing agents of the present invention may be used in any method in which a targeting species is used to deliver an active agent to a target site. For example they may be used in the direct targeting methods and pretargeting methods discussed above. The clearing agents of the present invention also may be used in the three- and four-step methods disclosed in U.S. Pat. Nos. 5,525,338 and 5,482,698 and Axworthy PCT Application No. WO 93/25240, the contents of which are herein incorporated by reference in their entirety.

In a direct targeting method, a species comprising the primary targeting moiety and the active agent is administered and allowed to localize. Then, a clearing agent according to the present invention is administered to remove non-localized circulating targeting species.

In a three-step pretargeting method, the primary targeting species is administered and allowed to localize. Then, the clearing agent is administered to remove non-localized primary targeting species. Then, the second targeting species is administered. For example, an antibody-biotin (or antibody-avidin) primary targeting species is administered and allowed to localized, followed by the administration of an anti-idiotype-antibody clearing agent according to the present invention. Then an avidin-active agent (or biotin-active agent) second targeting species is administered.

Using an anti-idiotype clearing agent in a biotin-avidin pretargeting system avoids the aforementioned disadvantages of known clearing agents. For example, since the clearing agent of one embodiment of the present invention does not contain biotin or avidin, none of the avidin-antibody conjugate localized at the target site is compromised by unwanted blocking of binding sites. Moreover, the anti-idiotypic second antibody clearing agent recognizes only the antigen-binding region (paratope) of the first antibody, hence the second antibody is capable of rapidly binding to circulating antibody, but is unable to bind to target-bound avidin-antibody conjugate and therefore is unable to remove avidin-antibody from the target.

Optionally, a cleavable biotin conjugate as noted above is added to bind avidin in the liver after the clearance step.

In a preferred embodiment of the present invention, the antibody-streptavidin targeting step and the anti-idiotype clearing step are followed by the injection of a monobiotinylated-dextran-(boron)$_x$ conjugate. Boron, as the B-10 isotope, is used for neutron capture reactions for therapy. Recently Holmberg and Meurling disclosed a method of attaching up to 1500 boron atoms per 70 kD dextran unit. Holmberg et al., *Bioconjugate Chem.* 4: 570–573 (1993). Such a unit attached directly to an antibody would significantly alter antibody properties. However, in itself it displays very attractive properties since it retains its water solubility. After limited biotinylation, such a monobiotinylated-dextran-(boron)$_{1500}$ species retains the solubility properties, and is capable of delivering up to 6000 boron atoms to the target, by virtue of the tetravalency of the streptavidin-IgG conjugate previously localized at the tumor. This is significantly more boron-10 than can be delivered by methods using IgG-polymer-boron-10 conjugates, which typically produce conjugates containing in the hundreds of boron atoms per antibody.

BNCT is a modality which has the singular advantage of being non-toxic to the host before neutron irradiation takes place. However, a poor target-to-non-targeted B-10 ratio negates much of this advantage, due to activation of non-targeted B-10 in the vicinity of the target. See, for example: Barth et al., *Cancer,* 70:2995–3007, 1992. In this instance the exquisite lethality of the emitted α-particles cause substantial unwanted tissue damage. In nude mouse xenograft models of radioimmunotheraphy using pretargeting, tumor-to-blood ratios at 24 h post-administration of biotinylated radiometal are in the 70-145:1 range, compared to below 5:1 in most systemic BNCT applications. Clearly, the current invention allows for substantially greater discrimination of tumor-to-blood ratios, in addition to the capacity for much enhanced total boron delivery described above.

U.S. Pat. Nos. 5,482,698 and 5,525,338, discussed above, describe targeting species, primary and second targeting moieties, and active agents which may be used in accordance with the present invention. For example, U.S. Pat. No. 5,482,698 sets forth antibodies, antibody fragments and other proteins which are useful as primary targeting moieties.

U.S. Pat. No. 5,482,698 also discloses radionuclides, para-magnetic ions and fluorescence-emitters which may be used as detection or therapeutic agents, as well as beta- and alpha-emitters and neutron-capturing agents, such as Boron and Uranium, which can be used as therapeutic agents.

Other therapeutic agents useful in accordance with the present invention include, drugs, fluorescent dyes activated by non-ionizing radiation, hormones, hormone antagonists, receptor antagonists, enzymes or proenzymes activated by another agent, autocrines or cytokines. Toxins also can be used in the methods of the present invention, such as plant and bacterial toxins, such as, abrin, alpha toxin, diphtheria toxin, exotoxin, gelonin, pokeweed antiviral protein, ricin, and saporin. Other therapeutic agents useful in the present invention include anti-DNA, anti-RNA, radiolabeled oligonucleotides, such as anti-sense oligodeoxy ribonucleotides, anti-protein and anti-chromatin cytotoxic or anti-microbial agents.

As set forth in U.S. Pat. No. 5,482,698, the targeting moiety may be conjugated to the active agent by methods known to those skilled in the art. U.S. Pat. No. 5,057,313, Shih et al., hereby incorporated by reference, teaches one method for conjugating biotin or avidin to an active agent.

Other examples of methods of conjugating avidin to a detection or therapeutic agent include the following: (a) the chloramine-T or Bolton-Hunter procedures for conjugating iodine, the latter being preferred; (b) the

TABLE 1

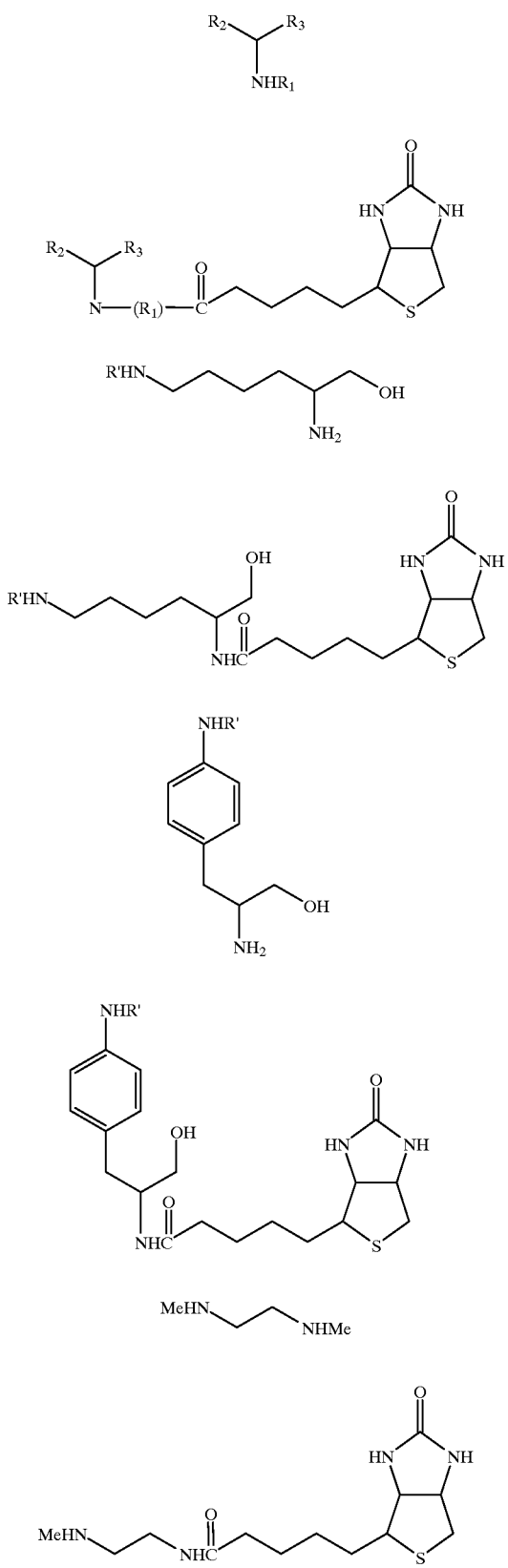

TABLE 1-continued

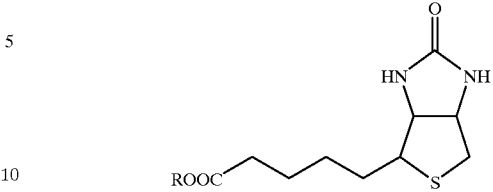

procedures described by Griffiths et al. (*Cancer Res.* 51: 4594, 1991) or Fritzberg et al. (U.S. Pat. No. 5,120,526) to conjugate technetium or rhenium; and (c) through bifunctional chelating agents as described by Meares et al. (*Br. J. Cancer* 62: 21, 1990) to conjugate metallic nuclides. Additionally, avidin or biotin can be bound to dendrimers by procedures described for amino-containing proteins as described by Hnatowich et al. (*J. Nucl. Med.* 28: 1294, 1987). Biotin can be readily conjugated to proteins (including antibodies and their fragments) via the proteins' lysine and cysteine residues, and, if available, their oxidized carbohydrate groups. Biotinylating agents are represented by the general formula II in Table 1, wherein $R_1$ is hydrogen, substituted alkyl, or substituted aryl group; $R_2$ is a group terminating in a primary or secondary amino group; $R_3$ is carboxyl, a substituted alkyl or substituted aryl group. Substituents on $R_1$ and $R_3$ can be, for example, carboxyl, tertiary amine such as dimethylamino or hydroxyl. These substrates can be prepared by reacting N-hydroxysuccinimidobiotin (see formula III in Table 1, wherein R=succinimidyl) with the appropriate amine of the general formula I in Table 1, wherein $R_1$, $R_2$ and $R_3$ have the same meaning as described above with reference to formula II.

The amine terminus of the biotinylated agents is suitably protected with a protecting group R', with R' being tertiary-butoxycarbonyl, for example, which is deprotected prior to the reaction with a metal-chelating agent or a boron-containing entity.

Some examples of the diamines which can be used for preparing biotinylating agents are shown as formulas Ia, Ib and Ic in Table 1.

Stability studies of various biotinylated chelates indicate that many are subject to the action of native biotinidase and that it is advantageous to link biotin to a chelator using a non-natural amino acid or other linker that is resistant to biotinidase. Suitable such linkers and biotinylated chelators are disclosed in copending U.S. patent application Ser. No. 08/688,781, which is incorporated herein by reference.

Many methods are known, as referenced above, for linking avidin or streptavidin (SA) to targeting moieties, especially antibodies. One preferred method is to partially reduce interchain disulfide bonds of an antibody or other protein, e.g., with mercaptoethylamine or a like disulfide reducing agent, to generate free sulfhydryl groups, which are then reacted with a derivative of streptavidin which bears a group that reacts with sulfhydryls. A particularly useful such function is a maleiimide, which can be linked to lysine residues of streptavidin using a bifunctional linker such as the commercially available sulfosuccinimidyl 4-(N-maleimido-methyl)cyclohexane-1-carboxylate (SMCC) to form SA-MCC. Once the conjugate is formed, by addition of sulfhydryls to maleimides to form thioethers, it is advantageous to cap unreacted sulfhydryls with, e.g., tetrathionate.

Antibody fragments, e.g., Fab or Fab' fragments, having free sulfhydryl groups, also can be linked to streptavidin using the SMCC linker, to form Fab-SA, (Fab)$_2$-SA, (Fab)$_3$-SA, (Fab)$_4$-SA, and the like, for use as primary targeting conjugates.

The present invention also may be used with other antibody-based pretargeting systems (i.e., those not utilizing biotin and avidin). For example, the specific hybridization of complementary DNA fragments may be used as the recognition mechanism of a pretargeting system. In such a method, one strand of DNA is bound to an antibody and the complementary strand is bound to a therapeutic radioisotope which is administered later. Bos et al., *Cancer Res.* 54: 3479–3486 (1994). A major advantage of this system over biotin/avidin systems could be the presumed lower immunogenicity of a relatively short piece of DNA compared to the highly immunogenic 60,000 Dalton avidin species.

In a further embodiment, synthetic DNA/RNA analogs may be used in the practice of the invention. Peptidyl nucleic acids (PNAs) are polypeptides such as polyserine, polythreonine, etc. including copolymers containing various amino acids, which are substituted at side-chain positions with nucleic acids (T,A,G,C,U). chains of such polymers are able to hybridize through complementary bases in the same manner as natural DNA/RNA. A single chain PNA bound to targeting antibody can be used in the current invention along with the complementary PNA strand bound to the diagnostic/therapeutic agent. In a preferred embodiment, peptidase-resistant PNAs are utilized, such as those prepared with D-amino acids.

Another approach to pretargeting involves administering an enzyme linked to an antibody, followed by administering a high-affinity enzyme inhibitor (specific for the enzyme) bound to a chelate-isotope complex. This method has the advantage over previous bispecific methods of retaining both antigen binding sites of the antibody, and the further advantage of utilizing a high affinity ($K_d$, dihydrofolate reductase:methotrexate=$10^{-10}$) secondary targeting mechanism. As with the DNA method discussed above, antigenicity may be less of a problem than in the avidin/biotin system.

A physiological solution of the targeting species is advantageously metered into sterile vials, e.g., at a unit dosage of about 1.0–500 mg targeting species/vial, and the vials are either stoppered, sealed and stored at low temperature, or lyophilized, stoppered, sealed and stored.

Variations and modifications of these formulations will be readily apparent to the ordinary skilled artisan, as a function of the individual needs of the patient or treatment regimen, as well as of variations in the form in which the radioisotopes may be provided or may become available.

Routes of administration for the composition include intravenous, intraarterial, intrapleural, intraperitoneal, intrathecal, subcutaneous or by perfusion.

Methods useful for internal detection and/or treatment of tumors and/or other lesions, such as cardiovascular lesions (clots, emboli, infarcts, etc.), infectious diseases, inflammatory diseases, and autoimmune diseases are disclosed in U.S. Pat. No. 4,782,840; U.S. Pat. No. 4,932,412; and co-pending U.S. application Ser. No. 07/879,857, which has been refiled and issued as U.S. Pat. No. 5,716,595, the disclosures of which are incorporated herein by reference. The methods of the present invention can be used to enhance the methods disclosed in these references. The present invention also may be practiced in conjunction with intraoperative probes, endoscopic and laparascopic uses, and in methods for imaging normal organs. The methods of the present invention can be used in other methods that will be apparent to those skilled in the art.

The methods of the present invention also can be practiced either with scintigraphic or magnetic resonance imaging agents, as described, for example, in Ser. No. 08/051,144.

The embodiments of the invention may be further illustrated through examples which show aspects of the invention in detail. These examples illustrate specific elements of the invention and are not to be construed as limiting the scope thereof.

EXAMPLES

Example 1

Preparation of Antibody-Streptavidin Immunoconjugates

In this procedure, streptavidin (SA) is substituted with a limited number of maleimido groups, and an IgG moiety is thiolated, after which the two components are mixed to effect protein conjugation.

A. Streptavidin-MCC

A thiol-reactive streptavidin is prepared by reacting streptavidin lysine residues with a limited amount of the S-N cross-linker, sulfo-succinimidyl 4-(N-maleimido-methyl) cyclohexane-1-carboxylate (sulfo-SMCC, Pierce Chemical Co., Rockford Ill.). Briefly, a solution of streptavidin (950 $\mu$l), containing 10 mg of streptavidin ($1.67\times10^{-7}$ mol) dissolved in 0.1 M borate buffer, pH 8.3, containing 10 mM EDTA, is treated with 35 $\mu$L of a freshly prepared solution of 10 mg/ml of sulfo-SMCC (FW 436.4; 350 $\mu$g; $8.03\times10^{-7}$ mol; 4.8 molar excess to SA). After 1 hour stirring at room temperature, the protein is purified from low MW materials on two G-50-80 size-exclusion spin-columns equilibrated in 0.1 M PBS, pH 6.4.

B. IMMU-14-SH

Two thiol groups are generated on INMU-14 IgG (anti-carcinoembryonic antigen antibody) (17 mg/mL) upon treatment in 17 mM 2-mercaptoethylamine containing 0.8 mM EDTA, pH 7.3, for 45 min at room temperature. IgG-SH is purified on centrifuged spin columns packed with SEPHA-DEX-G-50-80 in 0.1 M sodium phosphate, 5 mM EDTA, pH 7.

C. SA-IMMU-14 IgG

The SA-MCC product (1.1 ml) from Example 1A above is mixed with IgG-SH at 1:1 molar ratio. After stirring for 1 hour at room temperature, the unreacted sulfhydryl groups are blocked with 5 mM tetrathionate. Excess tetrathionate is removed on centrifuged spin columns prior to purification on a preparative size-exclusion HPLC column (Tosohaas, G3000SW). The conjugate is tested for its ability to bind In-111 labeled bio-DPTA and also biotinylated HSA. In both cases the conjugate shows binding to biotin.

Example 2

Preparation of Antibody Fragment-Streptavidin Immunoconjugates

In this procedure, streptavidin (SA) is substituted with a limited number of maleimido groups, and reacted with Fab-SH, after which the products, consisting of Fab-SA, (Fab)$_2$-SA, (Fab)$_3$-SA and (Fab)$_4$-SA, are separated on the basis of their size.

A. Fab-SH

IMMU-14-F(ab)$_2$ at 15 mg/ml (5 mg) is reduced with 20 mM cysteine, for 1 hour at 37° C., to give IMMU-14-Fab-SH. The progress of the reduction is followed by analytical size-exclusion HPLC. The IMMU-14-Fab-SH is separated from unreacted cysteine using a G-50-80 size-exclusion spin-column equilibrated with 100 mM PBS pH 7.4, containing 2 mM EDTA. The recovered protein concentration is calculated from measurement of the $\lambda_{280}$ absorbance of a small diluted aliquot of the product.

C. Fab-SA, (Fab)$_2$-SA, (Fab)$_3$-SA and (Fab)$_4$-SA

The two reaction products from Examples 1A and 2A above are mixed together and stirred 30 minutes at room temperature. The approximate molar ratios involved in this reaction are 1.75 mg streptavidin-MCC ($2.9\times10^{-8}$ Mol) and 5 mg IMMU-14 Fab ($1.0\times10^{-7}$ Mol), which is a 1:3.4 molar ratio of SA:Fab-SH. At the end of the 30 minute reaction, 5 μl of a 10 mg/ml freshly-prepared solution of cysteine.HCl (50 μg; $2.85\times10^{-7}$ Mol; 10-fold theoretical excess to SA-MCC; approximate concentration of 0.285 molar in cysteine, which is not enough to further reduce MAb) in water is added, and the stirring is continued at room temperature for a further 15 minutes in order to block any remaining unreacted maleimide residues. At the end of this 15 minute blocking reaction, the reaction mixture is purified by preparative size-exclusion HPLC, as described in Example 1. Samples are collected from the column in the order of decreasing molecular weight.

Example 3
Galactosylation of the Anti-Idiotypic WI2 Antibody

The WI2 antibody is described in Losman et al., *Int. J. Cancer* 56:580–584 (1994), the contents of which are incorporated by reference. It is an anti-idiotypic antibody to the murine anti-CEA mab, MN-14.

Proteins are glycosylated according to the method outlined by Ong et al., *Cancer Res.* 51: 1619–1626, (1991). Briefly, cyanomethyl-2,3,4,6-tetra-O-acetyl-1-thio-β-D-galactopyranoside (Sigma Chemical Co., St. Louis Mo.) is dissolved in dry methanol to give a 0.1 M solution and then mixed with a 1/10th volume of sodium methoxide (J. T. Baker Chemical Co., Phillipsburg N.J.). The flask contents are stoppered to prevent absorption of water, and then left to stand 48 hours at room temperature. The solution may be stored for a period of months in the refrigerator.

For conjugation to each mg of WI2 antibody, 500 μl of the imido ester solution is evaporated to dryness and then redissolved in a 1 mg/ml solution of WI2 in 0.25M sodium borate buffer, pH 8.5. After standing for 2 hours, the galactosylated WI2 is dialyzed into 0.1M phosphate buffered saline, pH 7.4.

Example 4
Preparation of Biotin-(Carborane)$_n$-Dextran Conjugate

A. Thiolated biotin

A solution of 5-(biotinamido)pentylamine (32.85 mg, 0.1 mM) in 100 μl 0.05 M borate buffer, pH 8.5, is stirred at room temperature and treated with a solution of 2-iminothiolane (13.76 mg, 0.1 mM) in 100 μl water. The mixture is incubated 30 minutes at room temperature and used immediately in reaction 4C below, or is aliquoted and frozen for future use.

B. (Allyl)$_n$-dextran

The boronation aspect of this procedure is the same as that described by Holmberg et al., *Bioconjugate Chem.* 4: 570–573 (1993). Dextran (20 g, 70,000 MW) is dissolved in 150 ml of distilled water containing 5 g of sodium hydroxide and 0.2 g of sodium borohydride, and treated with allyl bromide (35 g, 0.3 mol) at 40° C. The mixture is stirred for 3 hours at 60° C., neutralized with acetic acid, and the product is purified by repeat precipitation in ethanol prior to drying to constant weight.

C. Biotin-(carborane)$_n$-dextran

To 20 mg of this (allyl)$_n$-dextran ($2.5\times10^{-7}$ mol, approximate FW 80,000, approximately 220 allyl groups per dextran unit or $5.5\times10^{-5}$ mol allyl moiety) in 200 μl of water is added 30 mg sodium borocaptate, $Na_2B_{12}H_{11}SH$ (Boron Biologics, BSH, $1.4\times10^{-4}$ mol), 2 μl ($2\times10$ mol) of the above solution of 5-[(biotinamido)-4-pentyl-amidino]butanethiol prepared in Example 4A, and ammonium persulfate (20 mg). The reaction is stirred for 2 hours at 50° C., and the product, biotin-(carborane)$_n$-dextran, is purified from low molecular weight materials on G-50-80 size-exclusion spin-columns. The product is quantitatively analyzed for boron content by inductively coupled plasma atomic emission spectroscopy (ICP-AES). The ratio of biotin per dextran unit is determined by the agent's ability to bind to known diminishing amounts of radiolabeled streptavidin. Binding is detected by a shift in the radioactivity peak of the radioiodinated streptavidin to higher molecular weight, by size-exclusion HPLC utilizing an in-line radioactivity detector.

Example 5
Preparation of P-[5(-Biotinamido)Pentyl(Amino) Thioureayl]-2-Benzyl-Diethylenetriaminepentaacetic Acid (BPD)

5-(Biotinamido)pentylamine (50.7 mg, $1.54\times10^{-4}$ mol) is dissolved in 700 μl of 0.1 M sodium phosphate, pH 8.5, and treated with p-(isothiocyanato)-2-benzyldiethylene tri-aminepentaacetic acid (43 mg, $3.23\times10^{-5}$ mol). The pH is raised to 9 with approximately 300 μl of saturated sodium phosphate, and the reaction is incubated for 30 minutes at 37° C., while maintaining the pH at 9. The reaction mixture is filtered and the product (BPD) obtained in pure form using preparative reverse-phase HPLC, consisting of 3 tandemly coupled 40×100 mm Waters Prep-Pak RCM base columns. The columns are equilibrated for 10 minutes in 0.1% trifluoroacetic acid in water, and the desired product is eluted with a 10–30% gradient of 90% acetonitrile containing 0.1% trifluoroacetic acid, over 30 minutes, at a flow rate of 75 ml/minute.

Example 6
High Specific Activity Yttrium-90 Radiolabeling of BPD

A 5 mCi sample of Y-90 (supplied in 10 μl of 0.05 M hydrochloric acid) is treated with 100 μl of 0.5 M sodium acetate buffer, pH 6, followed by 250 μl of a solution of BPD in 0.05 M acetate buffer, pH 8.1. The radio-labeling is allowed to proceed for 30 minutes, prior to radioanalysis using size-exclusion HPLC. A quantitative incorporation of yttrium-90 into the BPD is obtained. The specific activity of this labeling is approximately 2000 mCi of yttrium-90 per mg of BPD.

Example 7
In Vivo Localization of Yttrium-90-BPD to Pretargeted Streptavidin-IMMU-14

Athymic nude mice are injected subcutaneously with sufficient GW-39 tumor cells (expressing carcinoembryonic antigen) to produce a 200–300 μg solid tumor xenograft at 10 days post-implantation. At this time, a 250 μg dose of streptavidin-IMMU-14 is administered per animal. As with the IMMU-14 antibody itself, the maximum amount of streptavidin-IMMU-14 is localized onto the target tumor at 3 days post-administration. Then a streptavidin-IMMU-14 blood-clearing dose of galactose-WI2 is given to each animal, causing essentially all remaining circulating streptavidin-IMMU-14 to be immediately bound to the galactose-WI2 and deposited into the liver. Two hours after this, Y-90-BPD is given to the animals. A saturating dose of the Y-90-BPD binds to the localized streptavidin-IMMU-14 at the tumor, while the bulk of the non-tumor-bound Y-90-BPD is excreted through the urine within a 2–4 hour period.

Example 8
Localization of Biotin-(Carborane)$_n$-Dextran to Pretargeted Streptavidin-IGG Athymic nude mice are injected subcutaneously with sufficient GW-39 tumor cells (expressing carcinoembryonic antigen) to produce a 200–300 μg solid tumor xenograft at 10 days post-implantation. At this time a 250 μg dose of streptavidin-IMMU-14 is administered per animal. As with the IMMU-14 antibody itself, the maximum amount of streptavidin-IMMU-14 is localized onto the target tumor at 3 days post-administration. Then a streptavidin-IMMU-14 blood-clearing dose of galactose-WI2 is given to each animal, causing essentially all remaining circulating streptavidin-IMMU-14 to be immediately bound to the galactose-WI2 and deposited into the liver. Two hours after this, a tumor-saturating dose of biotin-(carborane)$_n$-dextran is given to the animals, with the excess non-tumor-targeted biotin-(carborane)$_n$-dextran cleared from the circulation via the hepatobiliary and renal systems.

Example 9
Preparation of Biotinylating Agents

A. 2-Amino-6-N(t-Butoxycarbonyl)Amino-1-Hexanol (Formula Ia of Table 1, R'=t-BOC)

N(t-butoxycarbonyl)lysine was reacted with borane-tetrahydrofuran complex in tetrahydrofuran (THF), at temperatures not exceeding 10° C., in an argon atmosphere for a period of 1–2 hours. Excess borane is decomposed by careful addition of aqueous THF. The product is then refluxed with 5 M aqueous sodium hydroxide solution for a period of 18 h, cooled to room temperature, concentrated on a rotary evaporator to remove THF, and thoroughly extracted with chloroform. The chloroform extract is dried over anhydrous sodium sulfate, and evaporated to obtain the product (colorless liquid; 70% yield) in which the terminal N-protecting group is intact.

B. 2-(Biotinamido)-6-amino-1-hexanol (Formula IIa in Table 1, R'=H)

N-Hydroxysuccinimidylbiotin (Sigma Chemical Co., St. Louis, Mo.) is mixed with the amine of formula Ia (described above) in equimolar ratio in dimethylformamide containing one equivalent of triethylamine. The reaction mixture is stirred at room temperature for 18 h in an argon atmosphere. The reaction mixture is concentrated to a small volume under high vacuum, diluted with ether, and the precipitated product is washed with ether and 2-propanol, and dried to obtain a product of formula IIa wherein R'=t-BOC. Amine-deprotection is carried out by stirring with neat trifluoroacetic acid for 30–60 min. at room temperature, followed by isolation of the product of formula IIa wherein R'=H.

Example 10
Preparation of Biotinylated Dextran (Stepwise Approach)

Carboxypentyl-(allyl)$_n$-dextran is prepared by dissolving 1 g of (allyl)$_n$-dextranExample 4B) in 10 ml of 4M aqueous sodium hydroxide, heating with 3.0 g of 6-bromohexanoic acid at 60–80° C. for 3 h, and purifying the product by dialysis against water. The extent of carboxyalkylation is determined by titration with a standard solution of sodium hydroxide. 20 mg of carboxypentyl-(allyl) -dextran (dissolved in 0.2 ml of water) is boronated with 30 mg of sodium borocaptate at 50° C. for 2 h, as described in Example 4C, to obtain (carboxypentyl) m-dextran-(sulfhydrylborane)$_n$ where m and n refer to the number of carboxyalkyl and borocaptate groups introduced onto the dextran.

Using any of the biotinylating agents of the general formula II of Table 1, (carboxypentyl)$_m$-dextran-(sulfhydrylborane)$_n$ is derivatized using water soluble peptide coupling agent EDC [1-ethyl 3-(3-dimethylaminopropyl)-carbodiimide] and N-hydroxysulfosuccinimide. The number of biotin residues (most preferably one residue) introduced per dextran chain is controlled by the amount of biotinylating agent used in the reaction. Final molar substitution ratios are derived from determinations of boron-dextran ratio (from boron determinations), and biotin-dextran ratio (from determination of the extent of binding to known concentrations of streptavidin).

Table 2 illustrates the steps involved using one biotinylating agent. (The compounds in Table 2 are numbered independently of those of Table 1. The biotinylating agent 8 in Table 2 is the same as formula IIa (R'=H) of Table 1.)

TABLE 2

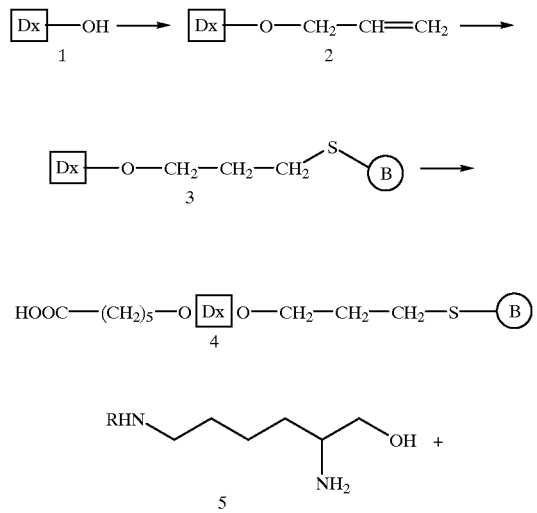

TABLE 2-continued
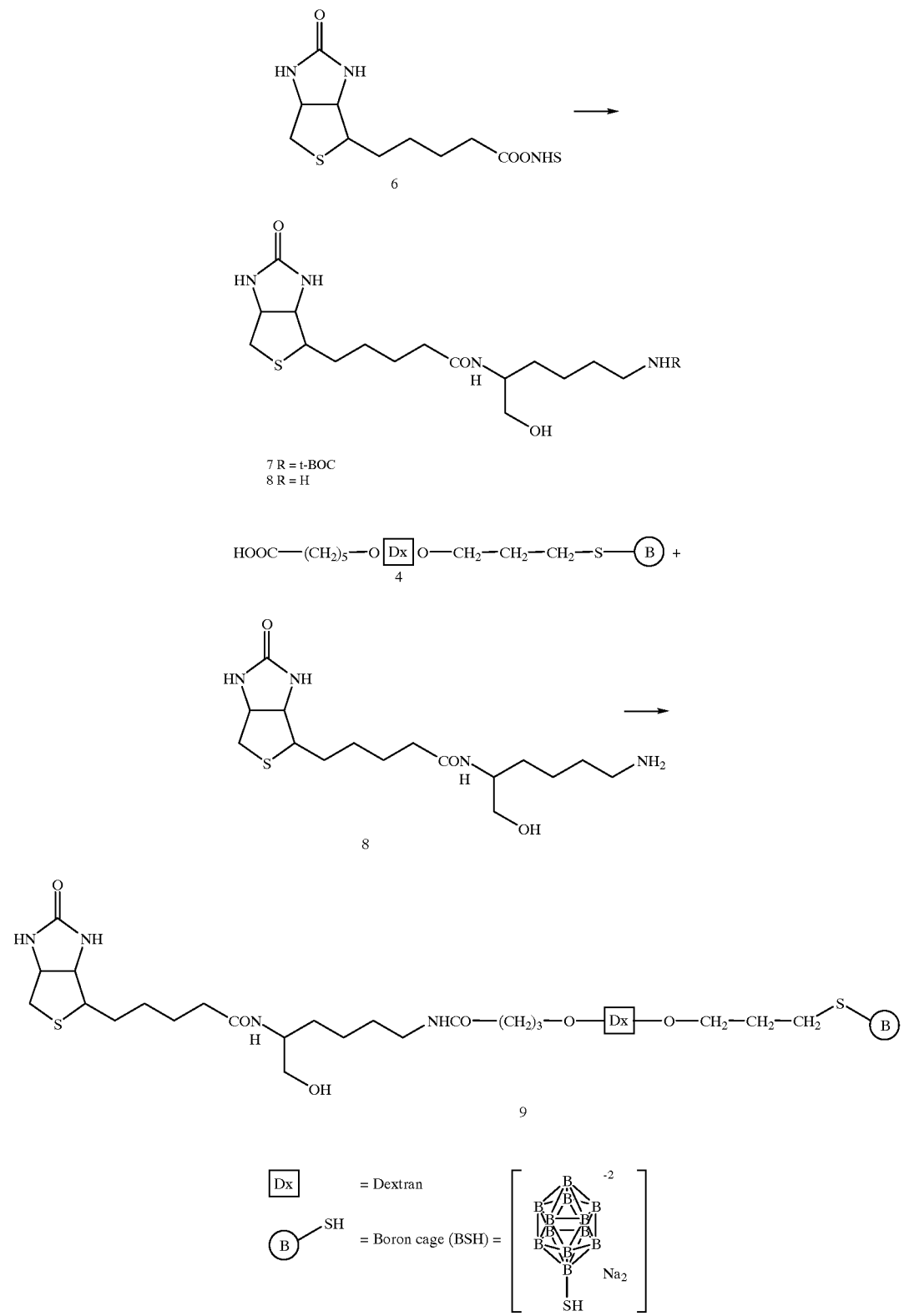

Example 11
Coupling a Biotinylating Agent of General Formula II with the Metal-Chelating Agent DOTA 1,4,7,10-Tetraazacyclododecane N,N',N",N'''-tetraacetic acid (DOTA) forms kinetically stable chelates with metal ions of lanthanide series (such as yttrium and gadolinium) of the periodic table. DOTA N-hydroxysulfosuccinimide ester is prepared following a known procedure (Lewis M. R., et al., *Bioconjugate Chem.*, 5: 565–576, 1994), by mixing 60 mg (128 μmol) of trisodium DOTA and 27.7 mg (28 μmol) of N-hydroxysulfosuccinimide, in 0.96 ml of water, and incubating this solution with 49 μl of a freshly prepared solution of 'EDC' (50 mg/ml) at 4° C. for 30 min. 1 ml of this solution contains 12.68 μmol (theoretical) of the mono-activated DOTA sulfosuccinimide.

An excess of this reagent is reacted with any of the amine-deprotected biotinylating reagent shown in Table 1, and stirred at 4° C. for a period of 18–24 hours. The biotinylated DOTA product is purified on a reverse phase preparative HPLC column using acetonitrile-water gradient-elution at a flow rate of 1 ml/min and monitoring the eluent with a refractive index detector. The purified material is analyzed by NMR spectroscopy and mass spectrometry.

Example 12
Targeting of Streptavidin-MAB [SA-IMMU-14]Conjugates to Tumor Xenografts This experiment is performed in order to determine the protein dose of SA-IMMU-14 which is necessary to saturate all available antigen binding sites in a tumor xenograft. Swiss nu/nu mice are injected subcutaneously in the back with sufficient cells of the GW-39 human tumor cell line to produce a solid tumor nodule of 100–200 mg at approximately ten days post-injection of cells. After tumors have grown to a suitable size, animals are split into groups of four to five per group and injected with increasing amounts of I-125-labeled-SA-IMMU-14 corresponding to 10 μg, 50 μg, 100 μg, 250 μg and 500 μg per [approximately] 20 g animal. Animals are anesthetized and euthanized at 24 hours post-injection of the I-125-SA-IMMU-14, and the major internal organs (liver, spleen, lung, kidney, blood and bone) as well as the GW-39 tumor xenograft are excised and counted for radioactivity content. From one experiment, the dose of SA-IgG required to saturate all available antigen tumor sites, for a tumor of this size, was determined to be about 250 μg of SA-IMMU-14 per animal.

Example 13
Investigation of Anti-Idiotypic Clearance of Circulating SA-IMMU-14.

Groups of animals, consisting of four to six nu/nu mice per group bearing GW-39 tumor xenografts produced as described in Example 12, are injected with 250 μg each of I-125-SA-IMMU-14. After 24 hours, groups of animals are given five-fold and ten-fold excesses of the radioidinated (I-131) anti-idiotype antibody WI2 or the radioiodinated (I-131) anti-idiotype antibody WI2 multiply substituted with residues of the monosaccharide D-galactose. A control group of animals is not given either WI2 moiety.

Groups of animals given the WI2 and the galactose-derivatized WI2, at both molar excesses, are taken and sacrificed at 1, 4, 24 and 48 hours post-injection of the anti-idiotype antibody. Organs are obtained as described in Example 12, and counted for radioactivity on a suitable counter through two separate channels, one set for the low energy emitter I-125, and the second channel set to read the high energy emitter I-131. Both antibodies exhibit a rapid clearance from the bloodstream of the I-125-SA-IMMU-14, with I-125-SA-IMMU-14 retained at the tumor xenograft. Other than at the tumor, most I-125 radioactivity is located in the liver, indicating that both species of WI2 at both dose levels are effective at clearing the circulating I-125-SA-IMMU-14. Animals not given clearing mab exhibit normal long-term retention of I-125-SA-IMMU-14 in the blood stream. Significant amounts of non-galactosylated WI2 remain in circulation out to 48 hours post-injection whereas essentially all galactosylated WI2 is cleared into the liver within 1 hour post-injection.

From this work, it is established that a five-fold excess of anti-idiotype antibody is sufficient to clear all circulating I-125-SA-IMMU-14, and that this amount of clearing nab does not substantially remove I-125-SA-IMMU-14 from the tumor. It is further established that the clearance of the targeting first antibody occurs very rapidly, within 1 hour. Finally, it is established that the galactose-WI2 is cleared from circulation very rapidly whereas the non-galactosylated WI2 circulated for the extended periods typical of a non-derivatized immunoglobulin.

Example 14
Delivery of Indium-111 to Tumor Xenografts Using a Pretargeting Protocol.

Swiss nu/nu mice bearing GW-39 tumor xenografts, produced as described in Example 12, are injected with I-125-SA-IMMU-14 followed 24 hours later by injection with a five-fold molar excess of galactosylated WI2 anti-idiotype mab. At 3 hours after the injection of the second antibody, three groups of 5–8 mice per group are given an injection of 10 μCi of 2 mCi/mg indium-111-labeled p-5-(biotinamido-pentyl(amino)thioureayl-2-benzyldiethylenetriaminepentaacetic acid (In-111-BPD). At 24 hours after the injection of the second antibody, two groups of eight animals each are given the same dose of In-111-BPD. A further three groups of animals are given In-111-BPD with no prior antibody injections. Animals given each of the three protocols are sacrificed at times corresponding to 1 hour (each protocol), 3 hours (In-111-BPD only protocol), 24 hours (each protocol), and 72 hours (first protocol, animals injected with gal-WI2 three hours after I-125-SA-IMMU-14) post-administration of the In-111-BPD. Collected tissues are again counted through dual windows on a suitable counter set for I-125 and In-111.

Animals given In-111-BPD without prior antibody injections exhibit very rapid clearance of indium from all of the above organs, and within 1 hour post-injection less than 1.8% of the injected dose remain in all organs combined. No tumor localization is seen in this group. Animals in protocol 1, injected with In-111-BPD three hours after injection of the gal-WI2 show greater tumor accumulation of both I-125-SA-IMMU-14 and In-111-BPD at both common sacrifice times (1 and 24 hour post-administration of In-111-BPD). Although absolute amounts of In-111-BPD in tumors is greater in the animals given the agent 3 h after administration of the gal-WI2 clearing mab, tumor/non-tumor ratios in both groups are comparable, with high tumor/blood ratios of In-111 of 5-6:1 and 12-25:1 seen at 1 hour and 24 hours post-injection of the In-111-BPD, respectively.

Example 15
Cure of Tumor-Bearing Nude Mice Using a Pretargeting Protocol.

Swiss nude (nu/nu) mice are injected sub-cutaneously in the back with sufficient cells of the GW-39 human tumor cell line to produce a solid tumor xenograft of 100–200 mg in size at approximately ten days post-injection of the cells. Animals bearing tumors of suitable size are split into five groups of 15–20 each and two of the groups are treated by intravenous injection with a 250 μg (a tumor-saturating) dose of SA-IMMU-14. A third group is given Y-90-IMMU-14, labeled in the normal manner by direct attachment of chelate to the antibody. After 24 hours, the two groups given the SA-IMMU-14 injection are given a five-fold molar excess of galactose-derivatized anti-idiotypic mab to IMMU-14 (gal.-WI2). After a further two hours, the animals in one of the groups of antibody-treated animals and the animals in one of the untreated groups of animals are given 50% of the maximum tolerated dose (determined empirically) of Yttrium-90-BPD.

The five groups of animals thus obtained are then as follows:
- Group 1—Untreated with any reagents.
- Group 2—Animals treated with the two cold antibodies SA-IMMU-14 and gal.WI2.
- Group 3—Animals treated with Y-90-BPD only.
- Group 4—Animals treated with the directly labeled Y-90-IMMU-14 reagent.
- Group 5—Animals treated with all three reagents; SA-IMMU-14, gal.-WI2 and Y-90-BPD.

Animals are tagged and returned to appropriate cages, fed and watered ad libitum, and measured for disease status biweekly. Animal weights are recorded and the sizes of the tumor xenografts measured using calipers. Within 6 weeks of implantation all animals in the untreated group (group 1) die due to their rapidly growing tumors. Animals in group 2, given just the cold antibodies, also die within 8 weeks post-injection. Animals in the group given just the Y-90-BPD reagent (group 3) also die this quickly since the isotope is not in the circulation for a long enough period of time to exert a non-specific radiation effect against the tumors. Animals in group 4 show a considerable improvement in overall survival time, out to 18–26 weeks post-implantation. This life extension is obtained at the cost of a considerable loss of weight (15–20% of body weight) in the first two to three weeks post-treatment with the Y-90-IMMU-14. The tumors regress after the treatment but resume their growth patterns after 15–20 weeks post-treatment, and the animals in this group eventually succumb to the tumors. Animals in group 5 are still alive at over 1 year post-treatment with full regression of tumors, no evidence of recurring tumor, and due to the specific nature of the therapeutic radiation delivered without the toxic effects typical of a long-circulating isotope, the animals in this group exhibit minimum weight loss.

Example 16
Cure of Tumor-Bearing Nude Mice Using an Alternate Protocol.

Swiss nude (nu/nu) mice are injected subcutaneously in the back with sufficient cells of the GW-39 human tumor cell line to produce a solid tumor xenograft of 100–200 mg in size at approximately ten days post-injection of the cells. Animals bearing tumors of suitable size are split into five groups of 15–20 each and two of the groups are treated by intravenous injection with a 250 μg (a tumor-saturating) dose of SA-IMMU-14. A third group is given Y-90-IMMU-14, labeled in the normal manner by direct attachment of chelate to the antibody. After 24 hours, the two groups given the SA-IMMU-14 injection are given a five-fold molar excess of anti-idiotypic mab to IMMU-14 (WI2). After a further two hours, the animals in one of the groups of antibody-treated animals and the animals in one of the untreated groups of animals are given 50% of the maximum tolerated dose (determined empirically) of Yttrium-90-BPD.

The five groups of animals thus obtained are then as follows:
- Group 1—Untreated with any reagents.
- Group 2—Animals treated with the two cold antibodies SA-IMMU-14 and WI2.
- Group 3—Animals treated with Y-90-BPD only.
- Group 4—Animals treated with the directly labeled Y-90-IMMU-14 reagent.
- Group 5—Animals treated with all three reagents: SA-IMMU-14, WI2 and Y-90-BPD.

Animals are tagged and returned to appropriate cages, fed and watered ad libitum, and measured for disease status biweekly. Animal weights are recorded and the sizes of the tumor xenografts measured using calipers.

Within 6 weeks of implantation all animals in the untreated group (group 1) die due to their rapidly growing tumors. A few animals in group 2, given just the cold antibodies survive longer than the group 2 animals from Example 15, due to the induction of an immune response by the long-circulating WI2 mab, but most die within 8 weeks post-injection. Animals in the group given just the Y-90-BPD reagent (group 3) also die quickly since the isotope is not in the circulation for a long enough period of time to exert a non-specific radiation effect against the tumors. Animals in group 4 show a considerable improvement in overall survival time, out to 18–26 weeks post-implantation. This life extension is obtained at the cost of a considerable loss of weight (15–20% of body weight) in the first two to three weeks post-treatment with the Y-90-IMMU-14. The tumors regress after the treatment but will resume their growth patterns after 15–20 weeks post-treatment, and the animals in this group eventually succumb to the tumors. Animals in group 5 are still alive at over 1 year post-treatment with full regression of tumors, no evidence of recurring tumor, and due to the specific nature of the therapeutic radiation delivered without the toxic effects typical of a long-circulating isotope, the animals in this group exhibit minimum weight loss.

Example 17
Treatment of Human Cancer Using a Pretargeting Procedure.

A patient presenting with a carcinoembryonic antigen (CEA)- producing cancer is treated with a 1 mg dose of I-131-SA-hIMMU-14 [SA-hIMMU14 is a conjugate corresponding to streptavidin-humanized (complementarity determining region-) cdr-grafted version of the IMMU-14 mab], labeled with 5 mCi of I-131 radionuclide (prepared by the iodogen method), in order to determine the localization qualities of the SA-hIMMU-14 conjugate.

With strong positive localization indicated from this initial injection, a 0.5 g dose of the SA-IMMU-14 is then infused over a 1 hour period using a sterile, non-pyrogenic, isotonic solution of the conjugate. After 24 hours post-injection of the targeting antibody conjugate, a 0.5 g first antibody-clearing dose of the galactosylated anti-idiotypic mab, gal.-hWI2, is infused in a similar manner. Two hours after administration of the hWI2, an infusion of 200 mCi of the therapy agent, Y-90-BPD, dissolved in 200 ml of phosphate buffered saline containing 1% v/v human serum albumin is begun. The patient is monitored for adverse reactions during the infusion of the isotope. After the infusion is complete, the patient's blood and urine are analyzed and quantified for the presence of radioyttrium out to 48 hours post-injection to determine the amount of isotope in circulation and the amount eliminated via the urine. The patient is observed periodically for the next two years, during which time is seen a complete response to the treatment.

Example 18
Treatment of Human Cancer Using an Alternate Procedure.

A patient presenting with a darcinoembryonic antigen (CEA)-producing cancer is treated with a 1 mg dose of I-131-SA-hIMMU-14 [SA-hIMMU14 is a conjugate corresponding to streptavidin-humanized (complementarity determining region-) cdr-grafted version of the IMMU-14 mab], labeled with 5 mCi of I-131 radionuclide (prepared by the iodogen method), in order to determine the localization qualities of the SA-hIMMU-14 conjugate. With strong positive localization indicated from this initial injection, a 0.5 g dose of the SA-IMMU-14 is then infused over a 1 hour period using a sterile, non-pyrogenic, isotonic solution of the conjugate. After 48 hours post-injection of the targeting antibody conjugate, a 0.5 g first antibody-clearing dose of the anti-idiotypic mab, hWI2, is infused in a similar manner. Four hours after administration of the hWI2, an infusion of 200 mCi of the therapy agent, Y-90-(2-biotinylmethylamidoethyl) methylamido-DOTA, dissolved in 200 ml of phosphate buffered saline containing 1% v/v human serum albumin is begun. The patient is monitored for adverse reactions during the infusion of the isotope. After the infusion is complete the patient's blood and urine are analyzed and quantified for the presence of radioyttrium out to 48 hours post-injection, to determine the amount of isotope in circulation and the amount eliminated via the urine. The patient is observed periodically for the next two years, during which time the cancer exhibits a full response to the treatment over this extended period of time.

(2-biotinylmethylamidoethyl)methylamido-DOTA:

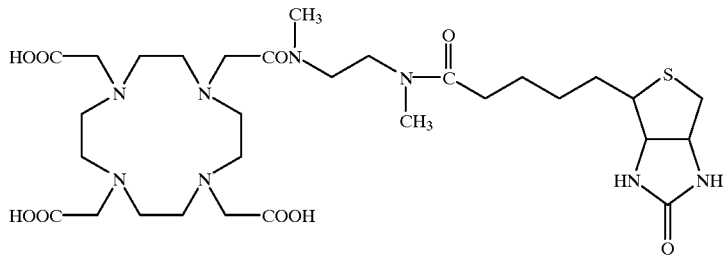

Example 19
Preparation of Biotinylated, Galactosylated Anti-Idiotypic WI2 Antibody In this procedure, W12 anti-idiotypic antibody is substitute with a limited number of galactose and biotin residues.

An imidate was prepared by the methods described in Mattes, *JNCI*, 4: 855–863 (1987) and Lee et al., *Biochem.*, 15(8): 3956–3963 (1976). Cyanomethyl 2,3,4,6-tetra-O-acetyl-1-thio-6-d-galactopyranoside (0.2315 g, $5.7 \times 10^{-4}$ mol) (Sigma Chemical Co., St. Louis, Mo.) was dissolved in 6.2 ml of anhydrous methanol. Sodium methoxide, 0.5 M in methanol, (115 ul, $5.75 \times 10^{-5}$ mol) was added to the above solution under argon and stirred at room temperature for 18 hours. Unused portion of imidate was stored at 4° C. and used as needed. Upon appearance of a precipitate, it was discarded.

Galactosylation:

WI2 (15 mg/ml) was applied to a centrifuged spin column, Sephadex G-50-80 in 0.1 M sodium phosphate, pH 8.1, to exchange the buffer. To conjugate 5, 10 and 22 galactose residues to WI2, imidate corresponding to 15, 30x and 75x molar excess of WI2, respectively, was evaporated with argon in individual vials. The oily residue was dissolved in WI2. The final protein concentration in each vial was adjusted to 8.4 mg/ml by addition of 0.1 M sodium phosphate, pH 8.1, and the final pH was adjusted to 8.5–8.6 with a saturated solution of tribasic sodium phosphate. The vials were stirred at room temperature for 2 hours. The modified WI2 was purified on two consecutive sets of centrifuged spin columns, Sephadex G-50-80 in 0.1 M sodium phosphate, pH 7.3.

To modify WI2 at 83–87% of its lysine residues, WI2 (5 mg/ml in 0.25 M sodium borate, pH 8.5) was treated with 1422x molar excess of dried imidate for 2 hours at room temperature. Treatment of WI2 (8.4 mg/ml in 0.1 M sodium phosphate, pH 8.1) with 100x, 300x and 500x molar excess of dried imidate at pH of 8.7 for 2 hours resulted in 78, 96 and 100% modification of lysine residues.

The extent of modification was determined by analyzing the degree of modification of protein primary amines using the fluorometric assay technique described by Stocks et al., Anal. Biochem. 23, 154: 232–234 (1986).

Biotinylation:

$Gal_{40}$-WI2 (13.3 mg., $8.6 \times 10^{-8}$ mol) in 0.1 M sodium phosphate, pH 8.1, was treated with 14 ul of 10 mg/ml solution of sulfo-NHS-LC-biotin (Pierce, Minneapolis, Minn.) ($2.6 \times 10^{-7}$ mol) in $H_2O$. Final protein concentration was adjusted to 14.7 mg/ml by addition of 0.1 M sodium phosphate (pH 8.1) and the pH was raised to 8.5 with a saturated solution of tribasic sodium phosphate. After 75 min at room temperature with occasional vortexing, the reaction mixture was applied to 3 consecutive sets of centrifuged spin columns, Sephadex G-50–80 in 0.1 M sodium phosphate (pH 7.3). The degree of modification was determined by analyzing the number of biotins using the procedure described by Green, Biochem J, 94: 230–240 (1965).

2.8biotins:

Treatment of WI2 with 6.5x molar excess of sulfo-NHS-LC-biotin rather than 3x as above at final protein concentration of 16.3 mg/ml at pH 8.6 for 90 min resulted in attachment of 2.8 biotins per WI2 molecule.

Example 20
Biotinylation and Galatosylation of Human Serum Albumin 0.7 biotins:

Human serum albumin (HSA) (Sigma Chemical Co., St. Louis, Mo.) was purified on a preparative size exclusion HPLC column to remove the high molecular weight contaminant. The purified protein was concentrated on Centricon 30 and buffer was exchanged to 8.1. Biotinylation was achieved by treating 60.5 mg purified HSA ($8.9 \times 10^{-7}$ mol) in 0.1 M sodium phosphate (pH 8.1) with 19.3 ul of 103 mg/ml solution of sulfo-NHS-LC-biotin ($4 \times 8.9 \times 10^{-7}$ mol) at a final protein concentration of 15 mg/ml at pH 8.5 adjusted with a saturated tribasic sodium phosphate solution. After 90 min at room temperature with occasional vortexing, the reaction mixture was applied to 3 sets of consecutive centrifuged spin columns to remove unreacted biotin. Biotin analysis showed 0.7 biotins per HSA.

1.6 biotins:

Bio$_{0.5}$-HSA was rebiotinylated to increase the number of biotins. Bio$_{0.5}$-HSA (42.9 mg, 6.3×10$^{-7}$ mol), was treated with 2.5x molar excess of sulfo-NHS-LC-biotin at final protein concentration of 15 mg/ml at pH 8.6 for 90 min at room temperature. The reaction mixture was applied to 3 sets of consecutive spin columns to purify the product. The number of biotins per HSA were determined to be 1.6.

Galactosylation:

Two batches of bio$_x$-HSA from above were treated with 100 and 300x molar excess of dried imidate (as prepared in Example 19) at a final protein concentration of 10 mg/ml in 0.1 M sodium phosphate at pH of 8.7, adjusted with a saturated solution of tribasic sodium phosphate. After 2 hours at room temperature with occasional vortexing, the conjugates were purified on two sets of spin columns. Fluorometric analyses showed about 45% and about 75% lysine modification per HSA for the 100 x and 300x, respectively.

Example 21

Effect of Galactose Substitution on WI2

WI2 was treated with excess thioimidate to introduce various levels of galactose (11, 22, 48 and 76% lysines modified). To determine the effect of galactose substitution, these proteins were radiolabelled with I-131 and injected into BALB/c mice. Animals were bled after 1 h and sacrificed 24 h post-injection. The amount present in blood at 1 h is shown in Table 3.

TABLE 3

% ID$^{131}$I-gal$_x$ WI2/g blood at 1 h

| % Modified lysines | % ID/g |
| --- | --- |
| 0 | 45.96 ± 5.203 |
| 11 | 51.19 ± 1.443 |
| 22 | 42.57 ± 2.545 |
| 48 | 5.92 ± 0.704 |
| ≧76 | 0.7 ± 0.2 |

TABLE 2

% ID$^{131}$I-gal$_x$ W12/g after 24 h

| | % ID/g | |
| --- | --- | --- |
| % Modified lysines | Blood | Liver |
| 0 | 22.81 ± 3.101 | 6.49 ± 1.394 |
| 11 | 23.31 ± 1.185 | 6.98 ± 0.798 |
| 22 | 17.04 ± 1.561 | 7.66 ± 0.752 |
| 48 | 3.26 ± 0.694 | 33.19 ± 2.335 |
| ≧76 | 0.2 ± 0.006 | 19.2 ± 7.0 |

It will be apparent to those skilled in the art that various modifications and variations can be made to the processes and compositions of this invention. Thus, it is intended that the present invention cover the modifications and variations of this invention provided they come within the scope of the appended claims and their equivalents.

We claim:

1. An in vivo pretargeting method for delivering a diagnostic or therapeutic agent to a target site in a mammal, comprising the steps of:

administering a primary targeting species to the mammal which binds via a primary, target-specific binding site to the target site or to a substance produced by or associated with the target site, and which comprises a peptidyl nucleic acid, and allowing the targeting species to localize at the target site;

administering a clearing agent that specifically binds to the primary binding site of the primary targeting species and allowing the clearing agent to clear the primary targeting species from circulation, whereby substantially only non-bound primary targeting species is cleared and targeted primary targeting species is not competitively removed from the target site, nor is the peptidyl nucleic acid of the primary targeting species blocked by the clearing agent, and wherein the clearing agent is an antibody or an antigen-binding fragment of an antibody, wherein at least about 48% of the lysine residues of the clearing agent are modified by introduction of galactose residues; and administering an active agent conjugate comprising a diagnostic or therapeutic agent conjugated to a complementary peptidyl nucleic acid that binds to the peptidyl nucleic acid of the primary targeting species.

2. The method of claim 1, wherein the peptidyl nucleic acid of the primary targeting species comprises at least one D-amino acid.

3. The method of claim 1, wherein the complementary peptidyl nucleic acid of the active agent conjugate comprises at least one D-amino acid.

4. The method of claim 1, wherein the primary targeting species comprises an antibody or antigen-binding antibody fragment.

5. The method of claim 4, wherein the clearing agent is an anti-idiotypic antibody or an antigen-binding fragment of an anti-idiotypic antibody.

6. The method of claim 1, wherein the active agent conjugate comprises a diagnostic agent.

7. The method of claim 6, wherein the diagnostic agent is selected from the group consisting of radionuclides, paramagnetic ions and fluorescence-emitters.

8. The method of claim 1, wherein the active agent conjugate comprises a therapeutic agent.

9. The method of claim 8, wherein the therapeutic agent is a radionuclide or neutron-capturing boron addend.

10. The method of claim 8, wherein the therapeutic agent is selected from the group consisting of drugs, toxins, fluorescent dyes, hormones, hormone antagonists, receptor antagonists, enzymes, proenzymes, autocrines and cytokines.

11. The method of claim 8, wherein the therapeutic agent is selected from the group consisting of anti-DNA cytoroxic agents, anti-RNA cytotoxic agents, radiolabeled oligonucleotide cytotoxic agents, anti-protein cytotoxic agents, anti-chromatin cytotoxic agents, anti-DNA antimicrobial agents, anti-RNA antimicrobial agents, radiolalbeled oligonucleolide antimicrobial agents, anti-protein antimicrobial agents and anti-chromatin antimicrobial agents.

12. The method of claim 1, wherein the primary targeting species is a non-antibody primary targeting species which preferentially binds marker substances that are produced by or associated with the target site.

13. The method of claim 12, wherein the primary targeting species is selected from the group consisting of small peptides, steroids, hormones, cytokines, and neurotransmitters.

14. A kit for the in vivo pretargeting of a diagnostic or therapeutic agent to a target site in a mammal, comprising:

a primary targeting species which binds via a primary, target-specific binding site to the target site or to a substance produced by or associated with the target site, and which comprises a peptidyl nucleic acid;

a clearing agent that specifically binds to the primary binding site of the primary targeting species and which does not block the peptidyl nucleic acid of the primary targeting species, wherein the clearing agent is an antibody or an antigen-binding fragment of an antibody, wherein at least about 48% of the lysine residues of the clearing agent are modified by introduction of galactose residues; and an active agent conjugate comprising a diagnostic or therapeutic agent conjugated to a complementary peptidyl nucleic acid that binds to the peptidyl nucleic acid of the primary targeting species.

15. The method of claim 1, wherein at least about 76% of the lysine residues of the clearing agent are modified by introduction of galactose residues.

16. The method of claim 1, wherein hepatic clearance is effected substantially in a single pass.

17. The method of claim 1, wherein the primary targeting species comprises a humanized antibody or an antigen-binding fragment of a humanized antibody.

18. The method of claim 8, wherein the primary targeting species comprises a humanized antibody or an antigen-binding fragment of a humanized antibody.

19. The method of claim 18, wherein at least about 76% of the lysine residues of the clearing agent are modified by introduction of galactose residues.

20. The kit of claim 14, wherein at least about 76% of the lysine residues of the clearing agent are modified by introduction of galactose residues.

21. The kit of claim 14, wherein the primary targeting species comprises a humanized antibody or an antigen-binding fragment of a humanized antibody.

22. The kit of claim 20, wherein the primary targeting species comprises a humanized antibody or an antigen-binding fragment of a humanized antibody.

23. The kit of claim 14, wherein the peptidyl nucleic acid of the primary targeting species comprises at least one D-amino acid.

24. The kit of claim 14, wherein the complementary peptidyl nucleic acid of the active agent conjugate comprises at least one D-amino acid.

* * * * *